United States Patent
Florin et al.

(10) Patent No.: US 7,813,535 B2
(45) Date of Patent: Oct. 12, 2010

(54) SYSTEM AND METHOD FOR FUSED PET-CT VISUALIZATION FOR HEART UNFOLDING

(75) Inventors: Charles Florin, Princeton, NJ (US); Romain Moreau-Gobard, Bangalore (IN)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1219 days.

(21) Appl. No.: 11/401,640

(22) Filed: Apr. 11, 2006

(65) Prior Publication Data

US 2006/0235294 A1 Oct. 19, 2006

Related U.S. Application Data

(60) Provisional application No. 60/672,679, filed on Apr. 19, 2005.

(51) Int. Cl.
*G06K 9/00* (2006.01)

(52) U.S. Cl. .......................... 382/128; 378/21

(58) Field of Classification Search ................ 382/100, 382/128, 130, 131, 132, 168, 171, 173, 174, 382/181, 190, 195, 206, 276, 277, 285, 286, 382/288, 259, 293, 294, 295, 296; 378/4, 378/8, 18, 19, 21, 23, 24, 25, 26, 27, 162, 378/164, 901; 600/407, 425; 128/920; 434/188, 434/211, 214; 345/418, 419, 424, 581, 582, 345/587, 619, 649, 650, 653, 654; 33/30.1, 33/300, 318, 320
See application file for complete search history.

(56) References Cited

U.S. PATENT DOCUMENTS

| | | | | |
|---|---|---|---|---|
| 5,588,033 A | * | 12/1996 | Yeung | 378/4 |
| 5,889,524 A | * | 3/1999 | Sheehan et al. | 345/419 |
| 6,160,924 A | * | 12/2000 | Lazar | 382/285 |
| 6,295,464 B1 | * | 9/2001 | Metaxas | 600/407 |
| 6,490,476 B1 | * | 12/2002 | Townsend et al. | 600/427 |

(Continued)

FOREIGN PATENT DOCUMENTS

WO WO 2005/078632 * 8/2005

OTHER PUBLICATIONS

Mattes et al., "PET-CT Image Registration in the Chest Using Free-Form Deformations", IEEE Transactions on Medical Imaging, vol. 22, No. 1, Jan. 2003.*

(Continued)

*Primary Examiner*—Andrew W Johns
*Assistant Examiner*—Tahmina Ansari
(74) *Attorney, Agent, or Firm*—Donald B. Paschburg; F. Chau & Associates, LLC (57) ABSTRACT

A method for fusing two digitized image datasets for 2-dimensional visualization of the heart, includes providing a first digitized image and a second digitized image, each image acquired from a different imaging modality and each comprising a plurality of intensities corresponding to a domain of points on a 3-dimensional grid, and wherein the first and second images have been registered, segmenting the heart in one of said digitized images, forming a 2-dimensional maximum intensity projection of a surface of said heart from each of said digitized images, and fusing said images by overlaying one 2-dimensional projection of said surface over the other 2-dimensional projection of said surface.

14 Claims, 5 Drawing Sheets

U.S. PATENT DOCUMENTS

| | | | |
|---|---|---|---|
| 6,529,206 B1* | 3/2003 | Ohki et al. | 345/619 |
| 7,024,027 B1* | 4/2006 | Suri et al. | 382/130 |
| 7,480,402 B2* | 1/2009 | Bar-Zohar et al. | 382/131 |
| 2003/0093004 A1* | 5/2003 | Sosa et al. | 600/544 |
| 2004/0064014 A1* | 4/2004 | Melvin et al. | 600/37 |
| 2004/0087853 A1* | 5/2004 | Fujisawa | 600/425 |
| 2004/0252870 A1* | 12/2004 | Reeves et al. | 382/128 |
| 2005/0058328 A1 | 3/2005 | Moreau-Gobard | |
| 2005/0105786 A1 | 5/2005 | Moreau-Gobard et al. | |
| 2005/0228250 A1* | 10/2005 | Bitter et al. | 600/407 |
| 2007/0036418 A1* | 2/2007 | Pan et al. | 382/131 |
| 2009/0161926 A1* | 6/2009 | Florin et al. | 382/128 |

OTHER PUBLICATIONS

Perlizzari et al., "Accurate Three-Dimensional Registration of CT, PET and/or MR Images of the Brain", Journal of Computer Assisted Tomography, 13(1)20-26, Jan./Feb. 1989.*

Mattes et al., "PET-CT Image Registration in the Chest Using Free-Form Deformations", IEEE Transactions on Medical Imaging, vol. 22, No. 1, Jan. 2003.*

* cited by examiner

SYSTEM AND METHOD FOR FUSED PET-CT VISUALIZATION FOR HEART UNFOLDING

CROSS REFERENCE TO RELATED UNITED STATES APPLICATION

This application claims priority from "Fused PET-CT Visualization for Heart Unfolding", U.S. Provisional Application No. 60/672,679 of Moreau-Gobard, et al., filed Apr. 19, 2005, the contents of which are incorporated herein by reference,

TECHNICAL FIELD

This invention is directed to the visualization of image data volumes in medical imaging and computer vision applications.

DISCUSSION OF THE RELATED ART

The advent of multimodality imaging scanners combining positron emission tomography (PET) and computed tomography (CT) has led to a new paradigm in image display and presentation that raises new challenges in workstation interpretation software, image navigation, and communication. The essence of multimodality imaging is the ability to overlay imaging information from different modalities in a visually compelling fashion. This is accomplished by combining functional and anatomic data into multidimensional views using color-encoding techniques that provide visual clues on the spatial distribution of image data. The multi-modality visualization brings an extra dimension to the diagnostics requiring both structural and functional data.

Special reconstruction software and image display programs are required to rescale the native images from different spatial resolutions into orthogonal or oblique reformatted planes in which data from PET images are color coded and superimposed on corresponding anatomic CT images. The color overlay technique allows the user to visually identify areas of high tracer activity and determine the underlying anatomic structure. Because of the multidimensional nature of the data, visualization requires interactive multidimensional navigation techniques that allow the viewer to move the visualization planes through three spatial directions. While CT provides anatomical information, such as the localization of the coronary arteries, PET scans of the heart can be used to determine blood flow to the heart muscle and help evaluate signs of coronary artery disease. The challenge now is to use the fused CT and PET volumes to create "fused" curved-MPR images and more advanced 2D projections, such as the technique disclosed in co-pending application "Heart unfolding for coronary visualization", U.S. Patent Application Publication No. 2005/0058328 of Romain Moreau-Gobard, filed Aug. 3, 2004, the contents of which are incorporated herein by reference.

The 3D visualization of cardiac images often requires human interaction to prepare the data and remove structures that do not belong to the heart, such as lungs, liver, ribs, etc. In order to improve the efficiency of the cardiologist's work and improve diagnostic precision, the aforementioned patent application describes surface unfolding specifically for the CT modality to improve visualization.

SUMMARY OF THE INVENTION

Exemplary embodiments of the invention as described herein generally include methods and systems for fusing PET and CT images in a single reformatted image for heart unfolding. This technique utilizes volume layers for visualizing the heart's surface and provides a new way to interact with multi-modality 3D volumes. According to an embodiment of the invention, a composite flat (2D) image of the surface of the heart is obtained from a CT volume after segmentating and "unfolding" of the surface. The same operation is repeated for the PET volume and the final image is obtained by fusing CT and PET information in a single reformatted colored MPR image. The resulting superimposed images help a physician to see the diagnostic information obtained from the PET scan in relation with the anatomical information from the CT scan, in conjuction with the heart unfolding representation.

According to an aspect of the invention, there is provided a method for fusing two digitized image datasets for 2-dimensional visualization of the heart, including providing a first digitized image and a second digitized image, each image acquired from a different imaging modality and each comprising a plurality of intensities corresponding to a domain of points on a 3-dimensional grid, and wherein the first and second images have been registered, segmenting the heart in one of said digitized images, forming a 2-dimensional maximum intensity projection of a surface of said heart from each of said digitized images, and fusing said images by overlaying one 2-dimensional projection of said surface over the other 2-dimensional projection of said surface.

According to a further aspect of the invention, one of said images is acquired from a positron emission tomography (PET) scan, and the other of said two images is acquired from a computed tomography (CT) scan.

According to a further aspect of the invention, the heart is segmented in the CT image.

According to a further aspect of the invention, the heart segmentation identifies the surface of the heart.

According to a further aspect of the invention, the method comprises forming a distance map that associates with each point in said heart a distance from said point to the surface of the heart.

According to a further aspect of the invention, the method comprises using said distance map to model the heart surface by a 3-dimensional ellipsoid.

According to a further aspect of the invention, the 3-dimensional ellipsoid is a bi-axial ellipsoid wherein a center is computed as a center of gravity G of all points located on a distance map isosurface of distance 0, a major axis Z is a vector $G_M$, where M is a point on said isosurface maximizing the length $|G_M|$, a minor axis X is a vector $G_N$, where N is a point on said isosurface minimizing the length $|G_N|$, and a third axis Y orthogonal to said axes Z and X.

According to a further aspect of the invention, forming said 2-dimensional maximum intensity projection comprises casting rays from said ellipsoidal surface into said heart to form said 2-dimensional projection, wherein an intensity of a point $I(X)=I(u,v)$ on said 2D projection is a normalized sum of each intensity, $I_n$ along the ray $$I(u, v) = \frac{1}{N} \sum_{0<n<N+1} I_n,$$

wherein said 2D-point X(u, v) is computed according to:

$$[-\pi, \pi][-\pi/2, \pi/2] \mapsto [0, w][0, H], (\varphi, \theta) \mapsto \left(u = \frac{w}{2\pi}\varphi, v = \frac{H}{\pi}\theta\right),$$

wherein φ∈[0,2π] and θ∈[0,π] are the longitude and latitude, respectively, for each point P(φ, θ) on the surface of said ellipsoid, According to a further aspect of the invention, the method comprises using a transverse Mercator projection for forming said 2-dimensional maximum intensity projection of said heart surface from said ellipsoid.

According to a further aspect of the invention, forming said 2-dimensional maximum intensity projection of said heart surface using said PET image comprises computing corresponding points on said heart surface in said PET image from said CT image using said registration, selecting points on the surface in said PET image, along with points slightly inside the heart and slightly outside the heart, and summing and averaging intensity values along rays cast through said selected points.

According to another aspect of the invention, there is provided a program storage device readable by a computer, tangibly embodying a program of instructions executable by the computer to perform the method steps for fusing two digitized image datasets for 2-dimensional visualization of the heart.

DETAILED DESCRIPTION OF THE PREFERRED EMBODIMENTS

Exemplary embodiments of the invention as described herein generally include systems and methods for fused PET-CT visualization for heart unfolding. This invention may, however, be embodied in many alternate forms and should not be construed as limited to the embodiments set forth herein.

Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present invention. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (i.e., "between" versus "directly between", "adjacent" versus "directly adjacent", etc.).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes" and/or "including", when used herein, specify the presence of stated features, integers, steps, operations, elements, and/or components, but do not preclude the presence or addition of one or more other features, integers, steps, operations, elements, components, and/or groups thereof.

As used herein, the term "image" refers to multi-dimensional data composed of discrete image elements (e.g., pixels for 2-D images and voxels for 3-D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R, the methods of the inventions are not limited to such images, and can be applied to images of any dimension, e.g. a 2-D picture or a 3-D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

With an increasing adoption of multimodal PET/CT imaging techniques in routine clinical work, new fused visualizations for heart-unfolded surfaces could make a difference for the accurate diagnostic of cardiovascular diseases. The unfolded 2D view of the heart nicely displays all the coronary arteries and heart peripheral vessels at one glance. This view is of particular interest for clinicians as they can study the structure as well as the inner anatomy of the vessels without interacting with the 3D volume, transfer functions, cropping planes, etc. Using this view, a clinician can quickly and accurately locate and quantify vessel pathologies.

Coronary arteries are responsible for feeding the heart muscles with oxygenated blood. If a disease alters the proper functioning of the coronary arteries, the result could be the death of certain tissues and be lethal. On the other hand, some vessel pathologies may completely block a coronary artery without having any effect on the heart functioning. In order to recognize those pathologies that require immediate concern, clinicians need to use PET imaging, and to link PET results to CT imaging. PET shows the chemical functioning or death of organs and tissues. With PET and CT overlaid on a heart-unfolded view, a clinician can immediately measure the seriousness of a coronary pathology, and link a particular pathology from a CT image to its effect on the functioning of the heart, as determined from a PET image.

Figure 2:
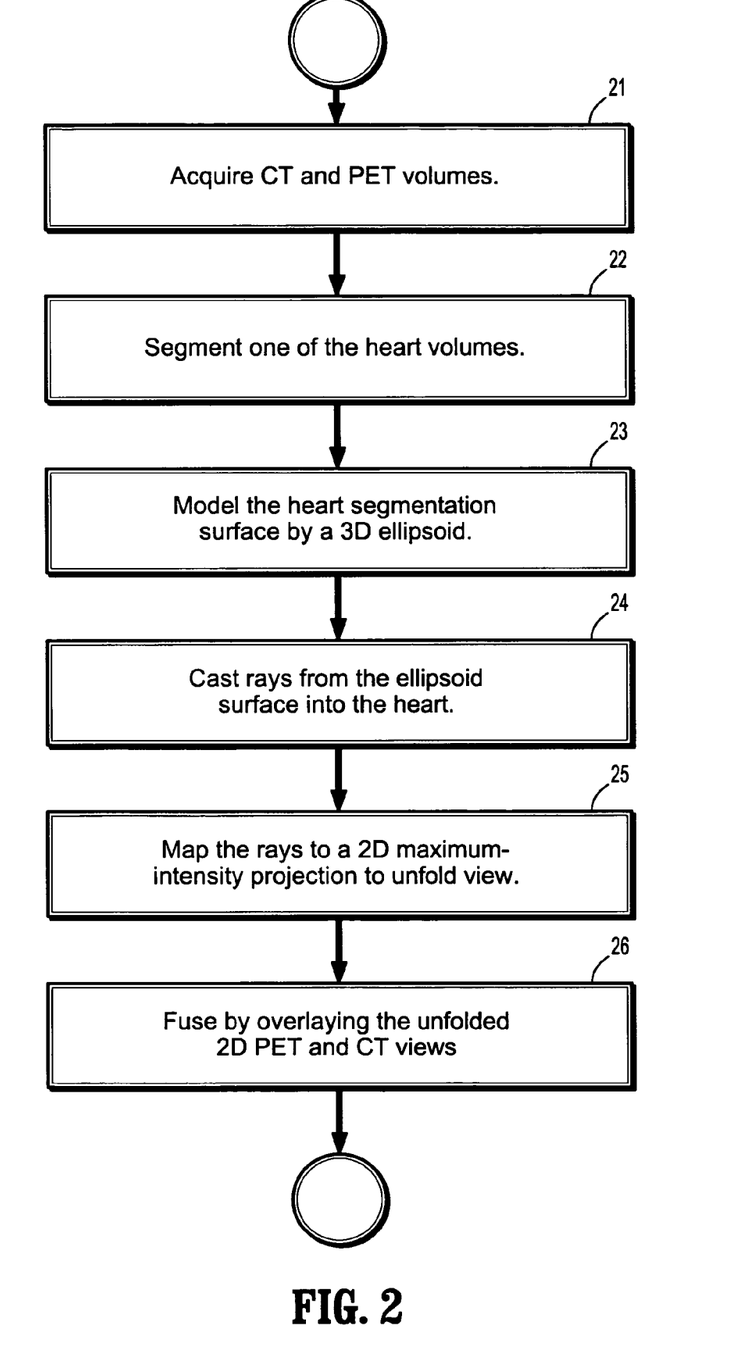
FIG. 2 is a flow chart of a method for fusing PET and CT images in a single reformatted image for heart unfolding, according to an embodiment of the invention.

A flow chart of an exemplary method for fusing PET and CT datasets for unfolding the surface of the heart is shown in FIG. 2, and includes the following steps. At step 21, PET and CT heart image data volumes are acquired. According to an embodiment of the invention, the images were acquired using a PET-CT scanner, and registration information can be included with the image data. One of the image volumes is segmented at step 22, and the heart surface is identified. The segmentation of the one image can be mapped onto the other image using the registration transformation. According to another embodiment of the invention, if no registration information is provided with the images, the heart surface is registered with the other image volume.

At step 23, the heart surface is modeled by a 3D ellipsoid. At step 24, rays are projected from the 3D ellipsoid to compute a 2D view of the heart surface. These the rays are mapped to a 2D maximum-intensity projection (MIP) to form an unfolded view at step 25. Note that steps 23, 24, and 25 can be performed for either the PET or CT datasets. The 3D coordinates for each ray can be saved and applied to the other image using the registration transformation between the two sets. Finally, at step 26, the 2D PET and 2D CT unfolded views are overlaid to from a fused 2D view. Although alternate 3D models and unfolding techniques may be used, some may adversely impact the quality of the results.

Note that although fusing of datasets is described in terms of PET and CT datasets, the methods described herein are applicable in other embodiments of the invention to the combination of image datasets acquired from any combination of imaging modalities, such as SPEC-CT and even MR-CT.

The next step is segmenting the heart volume. According to an embodiment of the invention, for practical reasons, it is better to work on the CT volume, and to use the registration correspondence between voxels in the CT volume and the PET volume to perform a corresponding segmentation of the PET data set. The main reason is the low spatial resolution of the PET data, reducing the precision of the segmentation, since the PET volume is acquired over multiple cardiac cycles, resulting in a blurry "blob" volume. A graph cut algorithm as known in the art, for example, may be used to segment the outer surface of the CT heart. This segmentation produces a 3D mask where pixels are labeled as object and background.

Figure 3:
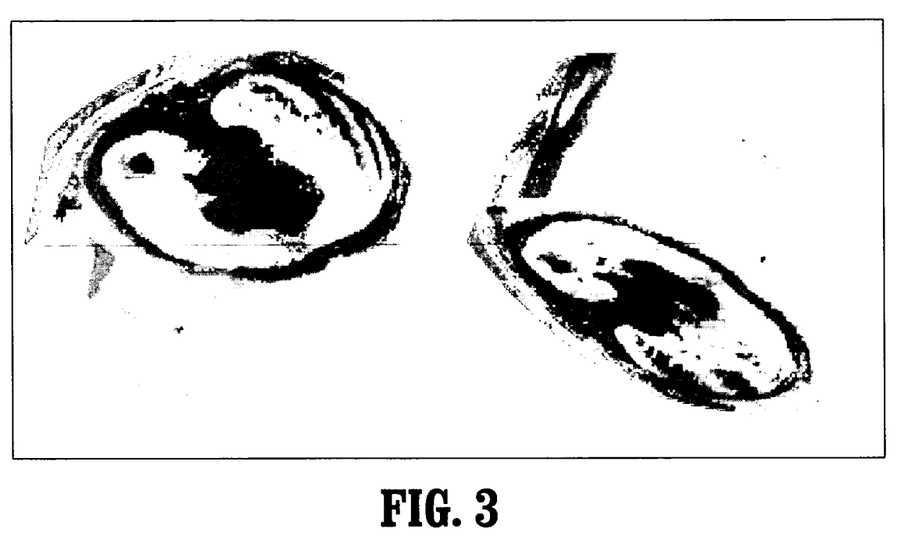
FIG. 3 depicts an exemplary view of a PET volume registered with a CT volume, according to an embodiment of the invention.

In order to fuse a PET data set and a CT data set, their coordinate systems need to be matched, since the two datasets are not always acquired using a common coordinate system. Therefore a 3D transformation needs to be performed to register the two data sets. There are many ways known in the art to specify a 3D transformation for registering two images, and any suitable transformation algorithm can be used to register the PET and CT data sets. As PET-CT volume registration algorithms become more and more efficient and widespread in the clinical world, the heart unfolding technique used for CT can now be used in parallel with PET. An exemplary view of a PET volume registered with a CT volume is shown in FIG. 3. A PET volume will frequently include registration data, as the same device is often used to generate both CT and PET volumes, in which case no additional registration step is needed. However, the better CT scanners, used for heart coronary diagnostic imaging, typically do not have PET capability, and therefore a registration is required. There are many possible registration methods for aligning two 3D "blobs". According to an embodiment of the invention, registration of the heart surface is performed by thresholding the PET volume and aligning the volume with the previously segmented CT heart surface.

From the result of this segmentation, a distance map is created to evaluate the distance from each point on the volume to the segmented surface of the heart. A distance map from the surface of the 3D mask can provide valuable constraints during the recovery of the peripheral vessels. For example, as the peripheral vessels stay parallel to the surface of the heart, their distance (i.e., distance of the vessels from the heart's surface) in the distance map varies smoothly. A distance map is basically a volume that associates to each point the distance between this point and a reference (in this case, the heart's surface). The segmented voxels are used to model the heart by a simpler geometrical object, such as an ellipsoid, to flatten its surface easily using cartography methods, as described in greater detail below.

The distance map is used to model the heart wall by an ellipsoid or a biaxial spheroid. Although one may consider a more accurate model such as a tri-axial ellipsoid, a major drawback is that no simple mathematical solution to the 3D-2D projection exists.

The biaxial ellipsoid projection is a well-known technique in cartography, but has only recently been applied to medical imaging of the heart. The biaxial spheroid reduces the deformations potentially occurring if using a sphere. For a biaxial ellipsoid of semi-axes length a and b, the surface equation is:

$$\frac{x^2}{a^2} + \frac{y^2}{a^2} + \frac{z^2}{b^2} = 1,$$

or, in a parametric form: $x=a\exists\cos(\phi)\sin(\theta)$, $y=a\exists\sin(\phi)\sin(\theta)$, $z=b\exists\cos(\theta)$, where $\phi\in[0,2\pi]$ and $\theta\in[0,\pi]$. Similar to what is commonly used in cartography, $\phi$ and $\theta$ are called the longitude and latitude, respectively. The ellipsoid center is computed as the center of gravity G of all the points located on the distance map isosurface 0 (the heart shell). The major axis Z is the vector $G_M$, where M is the point on the isosurface maximizing the length $|G_M|$. Similarly, the minor axis X is the vector $G_N$, where N is the point on the isosurface minimizing the length $|G_N|$. The axis Y is deduced to have a direct orthogonal base, $B=(G, X, Y, Z)$.

It should be noted that the quality of the modeling does not rely on the quality of the segmentation, which makes the method described herein independent from the selection of the segmentation method described above, and robust to noise. Moreover, unlike other organs, the heart naturally has the shape of an ellipsoid.

Figure 1:
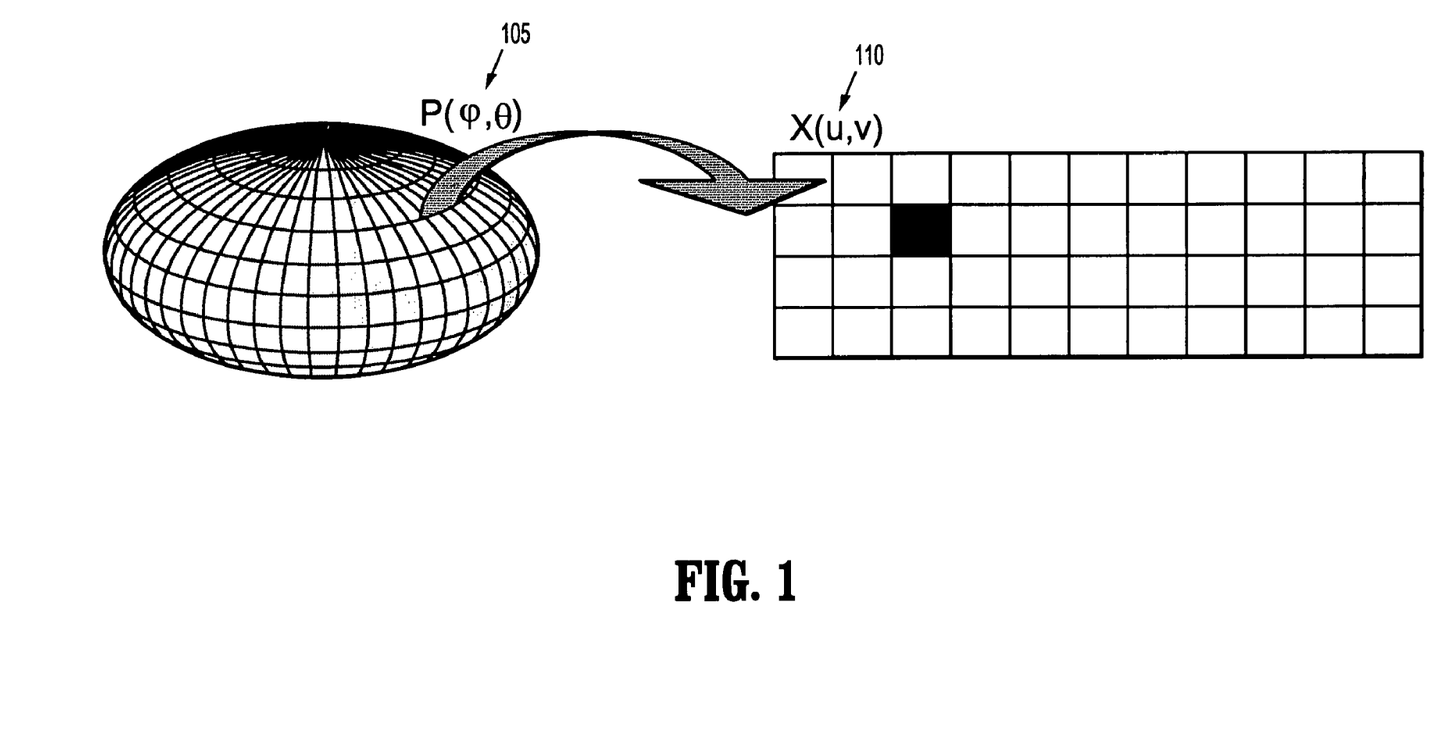
FIG. 1 depicts an exemplary mapping of a point from 3D space to a point in 2D space, in accordance with one exemplary embodiment of the present invention.

Next, rays are cast from the ellipsoid surface to compute a two-dimensional ("2D") view of the heart surface, and the intensities of the voxels crossed by the ray are collected. Each ray on the ellipsoid surface corresponds to a pixel on the 2D view. Therefore, the 2D view is painted by rendering each ray using a Maximum-Intensity Projection (MIP). The voxel intensities are collected in a predefined direction and range inside and outside the heart wall. The distribution of the nodes on the ellipsoid used to cast rays is computed through the following simple transformation. Referring now to FIG. 1, for each point P(φ,θ) 105 in a 3D-space (on an ellipsoid), the 2D-point X(u, v) 110 (on a plane) is computed according to:

$$[-\pi, \pi][-\pi/2, \pi/2] \mapsto [0, w][0, H], (\varphi, \theta) \mapsto \left(u = \frac{w}{2\pi}\varphi, v = \frac{H}{\pi}\theta\right).$$

Each pixel I(X)=I(u,v) on the 2D view is the normalized sum of each intensity, $I_n$, of the ray $$I(u, v) = \frac{1}{N} \sum_{0<n<N+1} I_n.$$

Note that if rays are cast directly from the distance map itself, the rays would not be homogeneous enough to be exploitable. Indeed, because of the heart surface irregularities, such rays would miss many vessels. Another solution may be based on a transverse Mercator projection for a biaxial ellipsoid. The drawback of such a method is that the volume has to be an ellipsoid of revolution, meaning the semi-minor axis is on the polar plane, and the semi-major axes are on the equatorial plane.

These steps of modeling the heart surface with an ellipsoid, casting rays from the surface, and mapping the rays onto a 2D MIP need not be performed for the PET dataset. The 3D coordinates of all the rays cast on the CT volume are saved. Using the registration correspondence formula between CT(X, Y, Z) and PET(X, Y, Z), one can obtain the intensities on the PET volume using the CT ray coordinates without having to perform the same complex set (segmentation, unfolding, ray casting) of operations.

Figure 4:
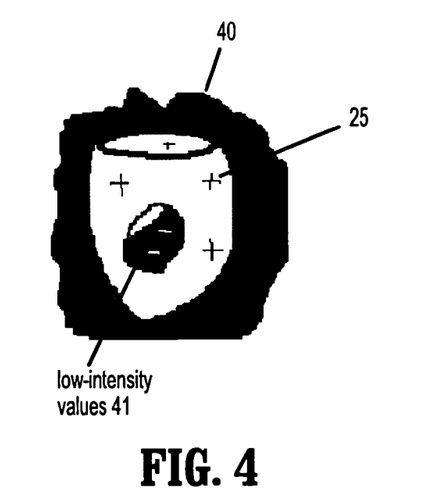
FIG. 4 depicts a schematic drawing of a PET scan of diseased heart, according to an embodiment of the invention.

Usually the PET volume has a "hole", formed by very low intensity values, where the diseased tissue is located. A schematic drawing of a PET scan of diseased heart is depicted in FIG. 4, where the low intensity values 41 of heart 40 are surrounded by high intensity values 42 of healthy heart tissue. According to an embodiment of the invention, intensity values that are on the surface of the 3D PET blob corresponding to the CT surface were considered, along with values slightly inside the heart and slightly outside the heart.

Since the information on the rays cast on the CT volume $\{X_{ct}, Y_{ct}, Z_{ct}, \text{Intensity}_{ct}\}$ is retained, the registration $\{X_{pet}, Y_{pet}, Z_{pet}\}$ can be computed to obtain the intensities on the PET volume. The intensities are then averaged to produce a single value. Note that PET is not a very accurate imaging modality, so it is acceptable to have a rough registration and rough intensity values for the surface. Usually the location of diseased tissue is quite obvious on a PET image volume.

Finally, at this stage, the 2D unfolded views from the PET data set and the CT data set can be overlaid, using the correspondences specified by the registration of the two 3D image volumes.

Figure 5:
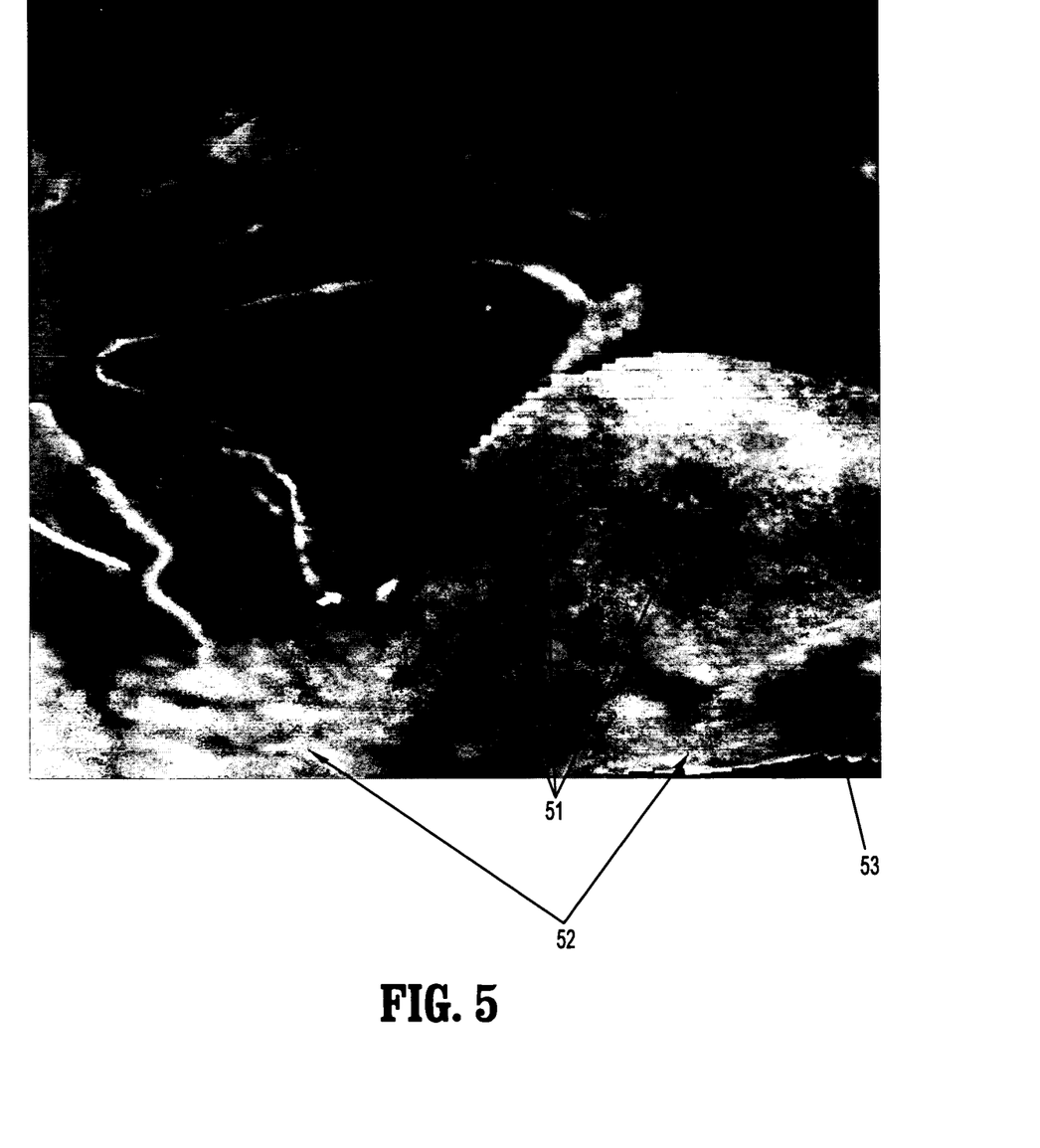
FIG. 5 depicts an example of an unfolded n-MIP view of the heart surface, according to an embodiment of the invention.

An example of an unfolded n-MIP (i.e., normal maximum intensity projection) view of the heart, resulting by fusing PET and CT views, is shown in FIG. 5. In this newly generated 2D flat surface of the heart, one can clearly see the parts feeding the heart muscles with oxygenated blood (51) and the parts that are not healthy (52, 53).

It is to be understood that the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 6:
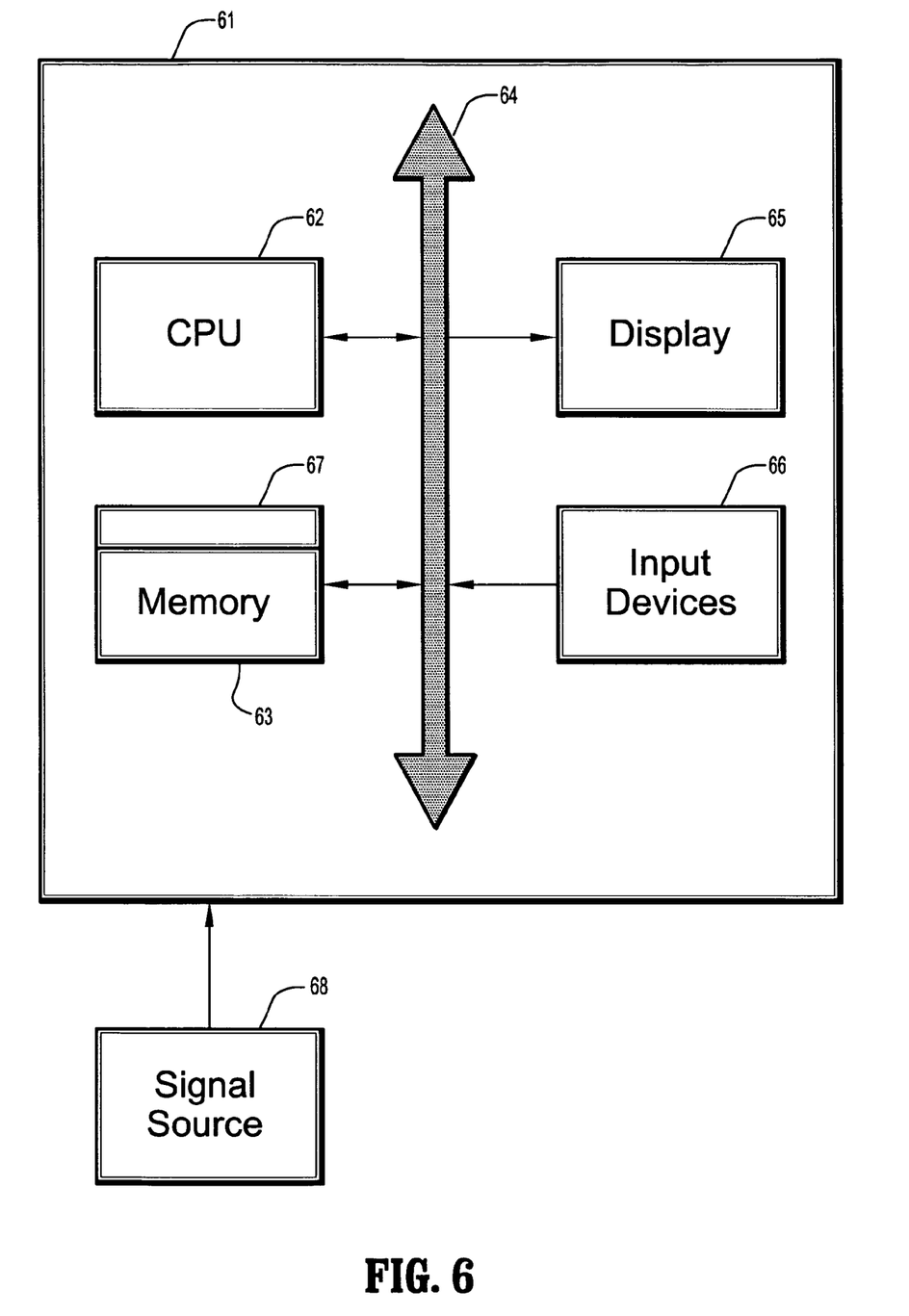
FIG. 6 is a block diagram of an exemplary computer system for implementing a method for fusing PET and CT images in a single reformatted image for heart unfolding, according to an embodiment of the invention.

FIG. 6 is a block diagram of an exemplary computer system for implementing a method for fusing PET and CT images in a single reformatted image for heart unfolding, according to an embodiment of the invention. Referring now to FIG. 6, a computer system 61 for implementing the present invention can comprise, inter alia, a central processing unit (CPU) 62, a memory 63 and an input/output (I/O) interface 64. The computer system 61 is generally coupled through the I/O interface 64 to a display 65 and various input devices 66 such as a mouse and a keyboard. The support circuits can include circuits such as cache, power supplies, clock circuits, and a communication bus. The memory 63 can include random access memory (RAM), read only memory (ROM), disk drive, tape drive, etc., or a combinations thereof. The present invention can be implemented as a routine 67 that is stored in memory 63 and executed by the CPU 62 to process the signal from the signal source 68. As such, the computer system 61 is a general purpose computer system that becomes a specific purpose computer system when executing the routine 67 of the present invention.

The computer system 61 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to a preferred embodiment, those skilled in the art will appreciate that various modifications and substitutions can be made thereto without departing from the spirit and scope of the invention as set forth in the appended claims.

What is claimed is:

1. A method of fusing two digitized image datasets for 2-dimensional visualization of the heart, comprising the steps of:

providing a first digitized image and a second digitized image, each image acquired from a different imaging modality and each comprising a plurality of intensities corresponding to a domain of points on a 3-dimensional grid, and wherein the first and second images have been registered;

segmenting the heart in one of said digitized images, wherein the heart segmentation identifies the surface of the heart;

forming a distance map that associates with each point in said heart a distance from said point to the surface of the heart;

using said distance map to model the heart surface by a 3-dimensional ellipsoid, wherein said 3-dimensional ellipsoid is a bi-axial ellipsoid wherein a center is computed as a center of gravity G of all points located on a distance map isosurface of distance 0, a major axis Z is a vector $G_M$, where M is a point on said isosurface maximizing the length $|G_M|$, a minor axis X is a vector $G_N$, where N is a point on said isosurface minimizing the length $|G_N|$, and a third axis Y orthogonal to said axes Z and X;

forming a 2-dimensional maximum intensity projection of a surface of said heart from each of said digitized images; and fusing said images by overlaying one 2-dimensional projection of said surface over the other 2-dimensional projection of said surface.

2. The method of claim 1, wherein one of said images is acquired from a positron emission tomography (PET) scan, and the other of said two images is acquired from a computed tomography (CT) scan.

3. The method of claim 2, wherein the heart is segmented in the CT image.

4. The method of claim 1, wherein forming said 2-dimensional maximum intensity projection comprises casting rays from said ellipsoidal surface into said heart to form said 2-dimensional projection, wherein an intensity of a point $I(X)=I(u,v)$ on said 2D projection is a normalized sum of each intensity, $I_n$ along the ray $$I(u,v) = \frac{1}{N} \sum_{0<n<N+1} I_n,$$

wherein said 2D-point X(u, v) is computed according to:

$$[-\pi, \pi][-\pi/2, \pi/2] \mapsto [0, w][0, H], (\varphi, \theta) \mapsto \left(u = \frac{w}{2\pi}\varphi, v = \frac{H}{\pi}\theta\right),$$

wherein $\phi \in [0, 2\pi]$ and $\theta \in [0, \pi]$ are the longitude and latitude, respectively, for each point $P(\phi, \theta)$ on the surface of said ellipsoid.

5. The method of claim 1, comprising using a transverse Mercator projection for forming said 2-dimensional maximum intensity projection of said heart surface from said ellipsoid.

6. The method of claim 3, wherein forming said 2-dimensional maximum intensity projection of said heart surface using said PET image comprises computing corresponding points on said heart surface in said PET image from said CT image using said registration, selecting points on the surface in said PET image, along with points slightly inside the heart and slightly outside the heart, and summing and averaging intensity values along rays cast through said selected points.

7. A method of fusing two digitized image datasets for 2-dimensional visualization of the heart, comprising the steps of:

providing a digitized computed tomography (CT) image and a digitized positron emission tomography (PET) image, each image comprising a plurality of intensities corresponding to a domain of points on a 3-dimensional grid;

segmenting the heart surface in said CT image;

modeling the heart surface with a 3-dimensional ellipsoid and forming a 2-dimensional maximum intensity projection of said heart surface from each of said digitized images, wherein forming a 2-dimensional projection of said heart surface from said CT image comprises casting rays from said ellipsoid into said heart to form a 2-dimensional projection of said heart surface, wherein an intensity of a point $I(X)=I(u,v)$ on said 2D projection is a normalized sum of each intensity, $I_n$ along the ray $$I(u,v) = \frac{1}{N} \sum_{0<n<N+1} I_n,$$

wherein said 2D-point X(u, v) is computed according to:

$$[-\pi, \pi][-\pi/2, \pi/2] \mapsto [0, w][0, H], (\varphi, \theta) \mapsto \left(u = \frac{w}{2\pi}\varphi, v = \frac{H}{\pi}\theta\right),$$

wherein $\phi \in [0, 2\pi]$ and $\theta \in [0, \pi]$ are the longitude and latitude, respectively, for each point $P(\phi, \theta)$ on the surface of said ellipsoid; and overlaying a 2-dimensional projection from said CT image over a 2-dimensional projection from said PET image.

8. The method of claim 7, further comprising registering said segmented heart surface from the CT image onto the PET image wherein correspondence formulae from the CT image to the PET image are obtained.

9. The method of claim 8, wherein coordinates of the rays are saved, wherein forming a 2-dimensional projection of said heart surface from said PET image comprises applying said correspondence formulae to said saved ray coordinates from said CT image to said PET image.

10. A program storage device readable by a computer, tangibly embodying a program of instructions executable by the computer to perform the method steps for fusing two digitized image datasets for 2-dimensional visualization of the heart, the method comprising the steps of:

providing a first digitized image and a second digitized image, each image acquired from a different imaging modality and each comprising a plurality of intensities corresponding to a domain of points on a 3-dimensional grid, and wherein the first and second images have been registered;

segmenting the heart in one of said digitized images, wherein the heart segmentation identifies the surface of the heart;

forming a distance map that associates with each point in said heart a distance from said point to the surface of the heart;

using said distance map to model the heart surface by a 3-dimensional ellipsoid;

using a transverse Mercator projection for forming said 2-dimensional maximum intensity projection of said heart surface from said ellipsoid for each of said digitized images; and fusing said images by overlaying one 2-dimensional projection of said surface over the other 2-dimensional projection of said surface.

11. The computer readable program storage device of claim 10, wherein one of said images is acquired from a positron emission tomography (PET) scan, and the other of said two images is acquired from a computed tomography (CT) scan.

12. The computer readable program storage device of claim 11, wherein the heart is segmented in the CT image.

13. The computer readable program storage device of claim 10, wherein said 3-dimensional ellipsoid is a bi-axial ellipsoid wherein a center is computed as a center of gravity G of all points located on a distance map isosurface of distance 0, a major axis Z is a vector $G_M$, where M is a point on said isosurface maximizing the length $|G_M|$, a minor axis X is a vector $G_N$, where N is a point on said isosurface minimizing the length $|G_N|$, and a third axis Y orthogonal to said axes Z and X.

14. The computer readable program storage device of claim 12, wherein forming said 2-dimensional maximum intensity projection of said heart surface using said PET image comprises computing corresponding points on said heart surface in said PET image from said CT image using said registration, selecting points on the surface in said PET image, along with points slightly inside the heart and slightly outside the heart, and summing and averaging intensity values along rays cast through said selected points.

* * * * *